US011473145B2

(12) United States Patent
De Lonlay-Debeney et al.

(10) Patent No.: US 11,473,145 B2
(45) Date of Patent: Oct. 18, 2022

(54) METHODS FOR DETERMINING WHETHER A PATIENT SUFFERING FROM RHABDOMYOLYSIS ACHIEVES A RESPONSE WITH A TLR9 ANTAGONIST

(71) Applicants: INSERM (INSTITUT NATIONAL DE LA SANTÉ ET DE LA RECHERCHE MÉDICALE), Paris (FR); FONDATION IMAGINE, Paris (FR); Université de Paris, Paris (FR); ASSISTANCE PUBLIQUE-HÔPITAUX DE PARIS (APHP), Paris (FR); CENTRE NATIONAL DE LA RECHERCHE SCIENTIFIQUE (CNRS), Paris (FR)

(72) Inventors: Pascale De Lonlay-Debeney, Paris (FR); Peter Van Endert, Paris (FR); Marine Madrange, Paris (FR); Yamina Hamel, Paris (FR); François-Xavier Mauvais, Paris (FR)

(73) Assignees: INSERM (INSTITUT NATIONAL DE LA SANTÉ ET DE LA RECHERCHE MÉDICALE), Paris (FR); FOUNDATION IMAGING, Paris (FR); ASSISTANCE PUBLIQUE-HÔPITAUX DE PARIS (APHP), Paris (FR); CENTRE NATIONAL DE LA RECHERCHE SCIENTIFIQUE (CNRS), Paris (FR); UNIVERSITÉ DE PARIS, Paris (FR)

( * ) Notice: Subject to any disclaimer, the term of this patent is extended or adjusted under 35 U.S.C. 154(b) by 223 days.

(21) Appl. No.: 16/633,912

(22) PCT Filed: Jul. 26, 2018

(86) PCT No.: PCT/EP2018/070256
§ 371 (c)(1),
(2) Date: Jan. 24, 2020

(87) PCT Pub. No.: WO2019/020732
PCT Pub. Date: Jan. 31, 2019

(65) Prior Publication Data
US 2021/0087633 A1 Mar. 25, 2021

(30) Foreign Application Priority Data

Jul. 27, 2017 (EP) ..................... 17306007

(51) Int. Cl.
*C12Q 1/68* (2018.01)
*C12Q 1/6883* (2018.01)
*C12Q 1/686* (2018.01)

(52) U.S. Cl.
CPC ......... *C12Q 1/6883* (2013.01); *C12Q 1/686* (2013.01); *C12Q 2600/106* (2013.01); *C12Q 2600/158* (2013.01); *G01N 2496/05* (2013.01); *G01N 2800/10* (2013.01); *G01N 2800/52* (2013.01)

(58) Field of Classification Search
CPC .................. C12Q 1/6883; C12Q 1/686; C12Q 2600/106; C12Q 2600/158; G01N 2496/05; G01N 2800/10; G01N 2800/52
See application file for complete search history.

(56) References Cited

U.S. PATENT DOCUMENTS

2018/0325890 A1* 11/2018 De Lonlay-Debeney ................... A61K 31/711

FOREIGN PATENT DOCUMENTS

WO 2017/085115 A1 5/2017
WO WO-2017085115 A1 * 5/2017 ........... A61K 31/365

OTHER PUBLICATIONS

Dimmock, D., Tang, L.Y., Schmitt, E.S. and Wong, L.J.C., 2010. Quantitative evaluation of the mitochondrial DNA depletion syndrome. Clinical chemistry, 56(7), pp. 1119-1127. (Year: 2010).*
Frisard et al., 2010. Toll-like receptor 4 modulates skeletal muscle substrate metabolism. American Journal of Physiology-Endocrinology and Metabolism, 298(5), pp. E988-E998. (Year: 2010).*
Hamel et al., 2015. Acute rhabdomyolysis and inflammation. Journal of inherited metabolic disease, 38(4), pp. 621-628. (Year: 2015).*

(Continued)

*Primary Examiner* — Teresa E Strzelecka
*Assistant Examiner* — Olayinka A Oyeyemi
(74) *Attorney, Agent, or Firm* — WCF IP

(57) ABSTRACT

The inventors initially participated to the identification of LPIN1 mutations as a cause for massive rhabdomyolysis episodes in children, triggered by febrile illness. The inventors have suggested that TLR9 antagonists would be suitable for the treatment of rhabdomyolysis (WO2017085115). The inventors thus treated 2 patients with lipin-1 disease by a TRL9 antagonist (hydroxychloroquine). They showed that the accumulation of mtDNA in plasma of the two patients before treatment decreases under treatment. When the treatment was stopped, the accumulation of mtDNA reappeared, then normalized when treatment was resumed. Accordingly, the present invention relates to a method for determining whether a patient suffering from rhabdomyolysis achieves a response with a TLR9 antagonist comprising determining the amount of mitochondrial DNA (mtDNA) in a blood sample obtained from the patient (e.g. by PCR).

5 Claims, 1 Drawing Sheet

(56) References Cited

OTHER PUBLICATIONS

Figure 1:
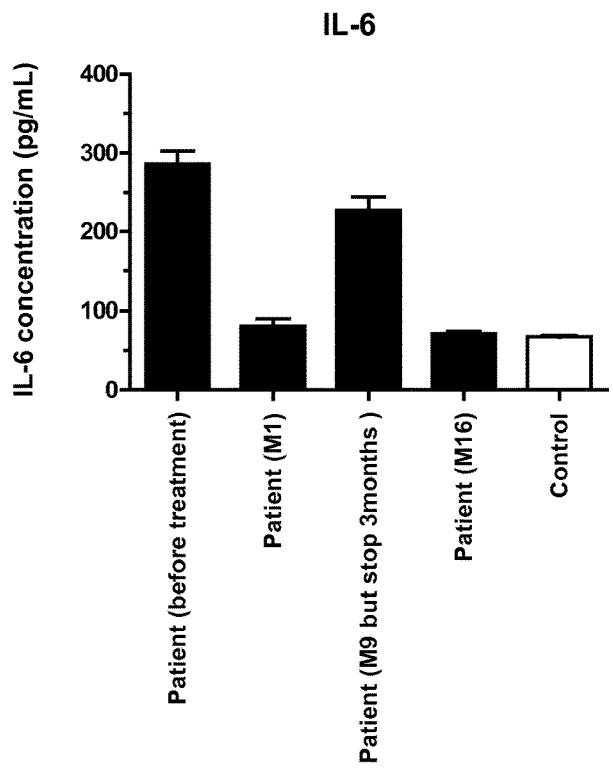

Kollberg et al., 2005. Mitochondrial myopathy and rhabdomyolysis associated with a novel nonsense mutation in the gene encoding cytochrome c oxidase subunit I. Journal of Neuropathology & Experimental Neurology, 64(2), pp. 123-128. (Year: 2005).*
Stringer, H., 2009. Mitochondrial DNA alterations and statin-induced myopathy (Doctoral dissertation, University of British Columbia). (Year: 2009).*
Stringer et al., 2013. Decreased skeletal muscle mitochondrial DNA in patients with statin-induced myopathy. Journal of the neurological sciences, 325(1-2), pp. 142-147. (Year: 2013).*
Yamanouchi, S., Kudo, D., Yamada, M., Miyagawa, N., Furukawa, H. and Kushimoto, S., 2013. Plasma mitochondrial DNA levels in patients with trauma and severe sepsis: time course and the association with clinical status. Journal of critical care, 28(6), pp. 1027-1031. (Year: 2013).*
Jean Bergounioux et al: "Fatal Rhabdomyolysis in 2 Children with Mutations", Journal of Pediatrics, Mosby-Year Book, St. Louis, MO, US, vol. 160, No. 6, Feb. 21, 2012, pp. 1052-1054.
Michot Caroline et al: "Combination of lipid metabolism alterations and their sensitivity to inflammatory cytokines in human lipin-1-deficient myoblasts", Biochimica et Biophysica Acta. Molecular Basis of Disease, vol. 1832, No. 12, Aug. 6, 2013, pp. 2103-2114.
J L Zimmerman: "Rhabdomyolysis", CHEST, vol. 144, No. 3, Sep. 1, 2013, pp. 1058-1065.
Avraham Zeharia et al: "Mutations in LPIN1 Cause Recurrent Acute Myoglobinuria in Childhood", American Journal of Human Genetics, vol. 83, No. 4, Oct. 1, 2008, pp. 489-494.

* cited by examiner

METHODS FOR DETERMINING WHETHER A PATIENT SUFFERING FROM RHABDOMYOLYSIS ACHIEVES A RESPONSE WITH A TLR9 ANTAGONIST

FIELD OF THE INVENTION

The present invention relates to methods for determining whether a patient suffering from rhabdomyolysis achieves a response with a TLR9 antagonist.

BACKGROUND OF THE INVENTION

The inventors initially participated to the identification of LPIN1 mutations as a cause for massive rhabdomyolysis episodes in children, triggered by febrile illness[1-5]. A third of patients die during acute rhabdomyolysis[5], often within hours of admission. At autopsy the inventors showed cardiomyopathy in two children, with accumulation of lipids and adipocytes in the heart[5]. However, cardiac explorations were normal in alive patients.

Lipin-1 is most abundantly expressed in adipocytes and skeletal muscle and plays a dual role i) as a phosphatidate acid phosphatase that contributes to triacylglycerol and phospholipid biosynthesis and ii) as a transcriptional coactivator associating with PPARα, SREBP1 and PGC-1α that regulates the expression of genes encoding proteins involved in Fatty Acid Oxidation in response to nutritional cues and the activation of the mTOR pathway ([10-15]).

The inventors' pioneer observation that a high level of pro-inflammatory cytokines can be detected in patient sera especially during flares has led them to test whether or not this may be explained by a preferential activation of a Pattern-Recognition Receptor (PRR), such as Toll-like Receptors (TLR). Exposing myoblasts and dendritic cells mutated for LPIN1 to various TLR agonists in vitro revealed a hypersensitivity of patient cells specifically to agonists of TLR9, an endosomal TLR that requires an activating cleavage by endolysosomal proteases. This intriguing phenotype was recapitulated by inactivating control cells for LPIN1. Wondering what could be the connections between the loss of enzymatic activity of lipin-1 enzyme and hyper-inflammation restricted to TLR9, the inventors first confirmed that cells deficient for lipin-1 exhibit reduced Vps34 PI-3K activity and consequently a decrease in phosphatidylinositol 3-phosphate (PI3P) specifically at the membrane of late endosomes. The inventors have thus suggested that TLR9 antagonists would be suitable for the treatment of rhabdomyolysis (WO2017085115).

SUMMARY OF THE INVENTION

The present invention relates to methods for determining whether a patient suffering from rhabdomyolysis achieve a response with a TLR9 antagonist. In particular, the present invention is defined by the claims.

DETAILED DESCRIPTION OF THE INVENTION

The inventors treated in 2016 two patients (P1, P2) with lipin-1 disease by hydroxychloroquine sulphate (plaquenil®) after obtaining the authorization by the CPP of Paris Descarte University (Comité pour la protection des personnes). They showed that the accumulation of mtDNA in plasma of the two patients before treatment decreases under treatment by Plaquenil®. After Plaquenil® was stopped, the accumulation of mtDNA reappeared, then normalized when treatment was resumed.

Accordingly, the first object of the present invention relates to a method for determining whether a patient suffering from rhabdomyolysis achieves a response with a TLR9 antagonist comprising i) determining the amount of mitochondrial DNA (mtDNA) in a blood sample obtained from the patient ii) comparing the amount determined at step i) with a predetermined reference value and iii) concluding that the patient achieves a response when the amount determined at step i) is lower that the predetermined reference value.

As used herein, the term "rhabdomyolysis" has its general meaning in the art and refers to rhabdomyolysis such as revised in the World Health Organization Classification M62.8, T79.5 and T79.6. The term "rhabdomyolysis" refers to a complex medical condition involving the rapid dissolution of damaged or injured skeletal muscle. This disruption of skeletal muscle integrity leads to the direct release of intracellular muscle components, including myoglobin, Creatine kinase (CK), aldolase, and lactate dehydrogenase, as well as electrolytes, into the bloodstream and extracellular space. Rhabdomyolysis ranges from an asymptomatic illness with elevation in the CK level to a life-threatening condition associated with extreme elevations in CK, electrolyte imbalances, Acute Renal Failure (ARF), and disseminated intravascular coagulation. Although rhabdomyolysis is most often caused by direct traumatic injury, the condition can also be the result of drugs, toxins, infections, muscle ischemia, electrolyte and metabolic disorders, genetic disorders such as Lipin-1 mutations, exertion or prolonged bed rest, and temperature-induced states such as Neuroleptic Malignant Syndrome (NMS) and Malignant Hyperthermia (MH). Massive necrosis, manifested as limb weakness, myalgia, swelling, and commonly gross pigmenturia without hematuria, is the common denominator of both traumatic and nontraumatic rhabdomyolysis (Torres et al., 2015; Zimmerman and Shen, 2013; Zutt et al., 2014). The term "rhabdomyolysis" also relates to juvenile forms of severe and recurrent rhabdomyolysis, which are inherited disorders characterized by the presence of myoglobinuria, high serum creatinine kinase levels and acute kidney injury [1, 2]. The term "rhabdomyolysis" also relates to Lipin-1 related rhabdomyolysis and Lipin-1 related juvenile forms of severe and recurrent rhabdomyolysis caused by LPIN1 mutations.

The method is thus particularly suitable for discriminating responder from non-responder. As used herein the term "responder" in the context of the present disclosure refers to a patient that will achieve a response, i.e. a patient where rhabdomyolysis is reduced or improved. Typically, the characterization of the patient as a responder or non-responder can be performed by reference to a standard or a training set. The standard may be the profile of a patient who is known to be a responder or non-responder or alternatively may be a numerical value. Such predetermined standards may be provided in any suitable form, such as a printed list or diagram, computer software program, or other media. When it is concluded that the patient is a non-responder, the physician could take the decision to modify the therapeutically effective amount of TLR9 antagonist (e.g. increasing the amount) or to stop the TLR9 antagonist therapy to avoid any further adverse sides effects.

The present invention is also suitable for monitoring compliance of the patient with the TRL9 antagonist wherein when an increase in the mtDNA is detected, it is concluded that the patient has failed to comply with the prescribed treatment.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "TLR9" has its general meaning in the art and refers to the Toll-like receptor 9, a member of a family of innate immune receptors, the TLRs which detect "danger signals", activate signaling pathways and induce inflammatory responses [37, 38, 39]. TLRs are present either at the cell surface or in endosomal compartments, the latter being the case for TLR9 [40]. The term "TLR9" also refers to CD289 (Cluster of Differentiation 289).

As used herein, the term "TLR9 antagonist" has its general meaning in the art and refers to a compound that selectively blocks or inactivates TLR9. As used herein, the term "selectively blocks or inactivates" refers to a compound that preferentially binds to and blocks or inactivates TLR9 with a greater affinity and potency, respectively, than its interaction with the other sub-types or isoforms of TLR family (such as TLR3, TLR7 and TLR8). Compounds that prefer TLR9, but that may also block or inactivate other TLR sub-types, as partial or full antagonists, are contemplated. The term "TLR9 antagonist" refers to any compound that can directly or indirectly block the signal transduction cascade related to the TLR9. The "TLR9 antagonist" may also consist in compounds that inhibit the binding of the TLR9 ligand CpG oligonucleotide (cytidine-phosphate-guanosine oligonucleotide) to TLR9 such as compounds having the ability to bind CpG oligonucleotide with high affinity and specificity or compounds that compete with CpG oligonucleotide. The term "TLR9 antagonist" also refers to inhibition of endosomal TLR9 activation by either inhibiting endosomal acidification, thereby preventing proteolytic maturation of endosomal TLRs, or by intercalation to nucleic acid ligands, thereby preventing their binding to TLRs. Typically, a TLR9 antagonist is a small organic molecule, an oligonucleotide, a polypeptide, an aptamer or an intra-antibody. Tests and assays for determining whether a compound is a TLR9 antagonist are well known by the skilled person in the art such as described in Hoque et al, 2013; Matin et al., 2015; Jiang et al., 2013; Kader et al., 2013; David et al., 2013; Kandimalla et al., 2013; Li et al., 2011; Wang et al., 2009; Yu et al., 2009; Zhang et al., 2010; Zhu et al., 2013; U.S. Pat. No. 7,498,409; WO 2005/007672; WO 2011/009015; WO 2012/022948; WO 2009/023819; WO 2011/041311; WO 2011/159958; and CN101712957. TLR9 antagonists are well-known in the art as illustrated by Hoque et al, 2013; Matin et al., 2015; Jiang et al., 2013; Kader et al., 2013; David et al., 2013; Kandimalla et al., 2013; Li et al., 2011; Wang et al., 2009; Yu et al., 2009; Zhang et al., 2010; Zhu et al., 2013; U.S. Pat. No. 7,498,409; WO 2005/007672; WO 2011/009015; WO 2012/022948; WO 2009/023819; WO 2011/041311; WO 2011/159958; and CN101712957. In some embodiments of the invention, the TLR9 antagonist is an oligonucleotide such as CpG ODNi (cytidine-phosphate-guanosine oligonucleotide inhibitors) such as CpG ODN 2088; CpG-ODN c41; IMO3100; IMO8400; IRS954 (DV1079); ALX-746-351; single-stranded phosphorothioate oligodeoxynucleotide antagonist such as DV056 and oligonucleotides described in Matin et al., 2015; Jiang et al., 2013; Kader et al., 2013; David et al., 2013; Kandimalla et al., 2013; Li et al., 2011; Wang et al., 2009; Yu et al., 2009; Zhang et al., 2010; Zhu et al., 2013; WO 2012/022948; WO 2009/023819; WO 2011/041311; WO 2011/159958; CN101712957. In some embodiments of the invention, the TLR9 antagonist is a compound, such as (−)-morphinans and (+)-morphinan derivatives such as COV08-0064; COV08-0093; nucleic acid binding polymers and other nucleic acid binding agents, including antimalarials such as chloroquine, primaquine and imidazoquinolines; 4-Amino-Quinolines; Quinazolines; CMZ 203-84; CMZ 203-85; CMZ 203-88; CMZ 203-88-1; CMZ 203-89; CMZ 203-91; aminoquinolines such as hydroxychloroquine and hydroxychloroquine sulfate (plaquenil®); quinacrine; bafilomycin A; CPG52364 and compounds described, for example in Hoque et al., 2013; WO 2005/007672; WO 2011/009015; WO 2012/022948; WO 2011/041311.

As used herein the term "blood sample" means a whole blood, serum, or plasma sample obtained from the patient. Preferably the blood sample according to the invention is a plasma sample. A plasma sample may be obtained using methods well known in the art. For example, blood may be drawn from the patient following standard venipuncture procedure on tri-sodium citrate buffer. Plasma may then be obtained from the blood sample following standard procedures including but not limited to, centrifuging the blood sample at about 1,500*g for about 15-20 minutes (room temperature), followed by pipeting of the plasma layer. Platelet-free plasma (PFP) will be obtained following centrifugation at about 13,000*g for 5 min. In order to collect or discard the microparticles, the plasma sample may be centrifuged in a range of from about 15,000 to about 20,000*g. Preferably, the plasma sample is ultra-centrifuged at around 17,570*g at a temperature of about 4° C. Different buffers may be considered appropriate for resuspending the pelleted cellular debris, which contains the microparticles. Such buffers include reagent grade (distilled or deionized) water and phosphate buffered saline (PBS) pH 7.4. Preferably, PBS buffer (Sheath fluid) is used. More preferably, the blood sample obtained from the patient is a platelet free platelet sample (PFP) sample. PFP may be separated from 10 ml citrated whole blood drawn from the fistula-free arm, 72 hours after the last dialysis. PFP may be obtained after citrate blood centrifugation at 1500*g (15 min), followed by 13000*g centrifugation (5 min, room temperature).

The quantification of the mtDNA in the blood sample may be performed by method well known in the art. In some embodiments, the quantification is performed by immunofluorescence (IF). In some embodiments, the quantification involves polymerase chain reaction (PCR). The method of the invention can include PCR assays, such as semi-quantitative or quantitative PCR or RT-PCR, optionally involving a coamplification of a mitochondrial sequence and a reference sequence, such as a nuclear sequence. The method of the invention may also include hybridization assays, for example, RNA or DNA hybridization assays, using mitochondrial and nuclear DNA or RNA samples in mitochondrial and reference sequences as probes. The method of the invention may also include quantification methods utilizing antibodies directed against mtDNA sequences, dyes or other labels intercalating into or absorbing onto mtNA DNA. Methods of quantitative PCR are for example disclosed in the following documents, all of which are incorporated herein by reference: U.S. Pat. Nos. 6,180,349; 6,033,854; and 5,972,602; Song, J. et al. (2001) Diabetes Care 24:865-869. A mitochondrial DNA sequence may be chosen from any mitochondrion-specific nucleotide sequence, including but not limited to ATP synthase 6, GenBank Accession No. AF368271; tRNA-Leu, GenBank Accession No. S49541; NADH dehydrogenase subunit 5 (MTND5), GenBank Accession No. AF339085; cytochrome b, GenBank Accession No. AF254896, or any other suitable any mitochondrion-specific nucleotide sequence. Amplification probes may be designed according to methods known in the art and described, for example, in Sambrook, et al. (Molecular Cloning: A Laboratory Manual. 3rd ed., Cold Spring Harbor Laboratory, Cold Spring Harbor Laboratory Press, Cold Spring Harbor, N.Y., 2001) or Ausubel et al. (Current Protocols in Molecular Biology, John Wiley & Sons, 1994). Alternatively, hybridization techniques may be employed to determine the presence or amount of mtNA in the sample. Suitable techniques using oligonucleotides or polynucleotides under stringent conditions are known to the skilled person. Preferably, the oligonucleotides or polynucleotides used as probes specifically hybridize with mtNA sequences. The amount of mtNA may further be determined by using polypeptides or carbohydrate ligands specifically recognizing mtNA, e.g. mtDNA. For example, antibodies recognizing hypomethylated DNA can be used in immunological assays that are known per se such as an ELISA. In some embodiments, an enzyme may be used which specifically targets hypomethylated DNA. For example, the enzyme may specifically cut hypomethylated DNA. At such "nick" sites a non radioactive label (e.g. biotin) or a radiolabel could be attached. Such label can then be quantified. In some embodiments, mtNA may first be isolated specifically from a pool of different nucleic acids and contaminants, for example by means of density gradient centrifugation. In a second step mtNA may then be quantified with any unspecific nucleic acid quantification method.

Typically, the predetermined reference value is a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement of the amount of mtDNA in properly banked historical subject samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the expression amount of mtDNA in a group of reference, one can use algorithmic analysis for the statistic treatment of the amounts determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1−specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

The invention will be further illustrated by the following figures and examples. However, these examples and figures should not be interpreted in any way as limiting the scope of the present invention.

FIGURES

FIG. 1. Inflammatory profile in serum of lipin-1 deficient patients in vivo. Above: IL-6 secretion in serum was measured by ELISA. IL-6 concentration decreases under treatment by Plaquenil® then increases after interruption of treatment then decreases again when the treatment is resumed.

Figure 2:
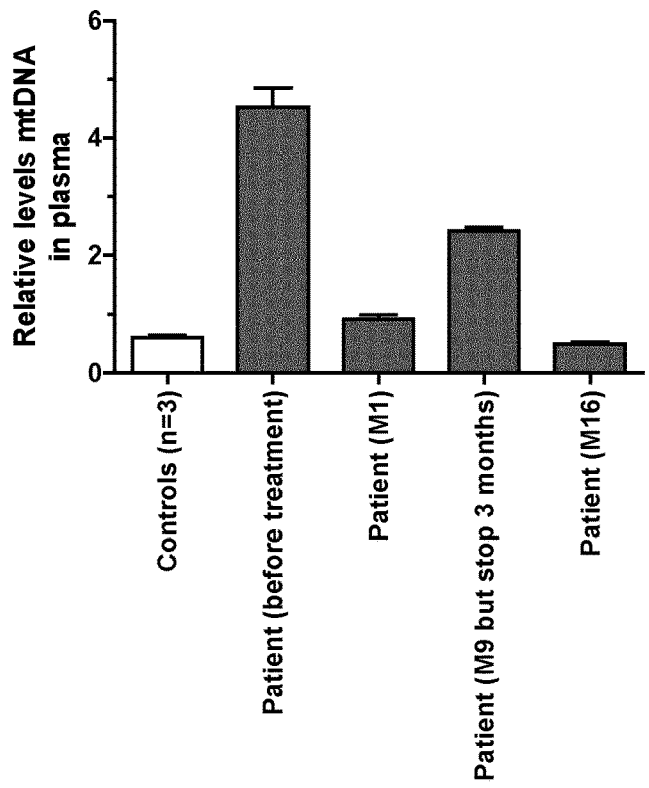

FIG. 2. Quantity of mitochondrial DNA (qPCR) in plasma of two patients. The accumulation of mtDNA before treatment in plasma decreases under treatment by Plaquenil® then increases after interruption of treatment then decreases again when the treatment is resumed.

EXAMPLE

We treated in 2016 two patients (P1, P2) with lipin-1 disease by hydroxychloroquine sulphate (plaquenil®) and two patients (P3, P4) with dantrolene sodium after obtaining the authorization by the CPP of Paris Descarte University (Comité pour la protection des personnes). Moreover the 16-year-old patient (P5) has been treated for one month by plaquenil® because of his cardiac dysfunction, his fatigability and his sleep disorders. Indeed we think that plaquenil® works well on the two patients treated (P1, P2) and P5's state was considered sufficiently serious to propose it. Plaquenil® was given at a dose of 6 mg/Kg/day into 1 intake (dose usually given in Lupus disease) to P1, P2 and P5.

Both patients 1 and 2 treated in vivo with Plaquenil® normalized their serum inflammatory profile in one month after the start of treatment (FIG. 1). IL-6 secretion increased in plasma when the two patients stopped their treatment (FIG. 1). The accumulation of mtDNA in plasma of the two patients before treatment decreases under treatment by Plaquenil® (FIG. 2). After Plaquenil® was stopped, the accumulation of mtDNA reappeared, then normalized when treatment was resumed. We observe a correlation between variations of IL-6 and mtDNA accumulation levels, and with the compliance of the treatment. Both patients also decreased the level of serum Creatine kinase (CK) and did not have any new episode of rhabdomyolysis during 6 months.

Patient 1 corrected his clinical muscle phenotype (Table 1). Physical maximum capacities were measured using six-minute walk (TC6'), Short-Form life quality by using Questionary (SF-36) to assess QOL for parent and for patient, and a self-assessment pain scale (EVA). For patient 2, the pain disappeared but the walking ability did not improve markedly. After 6 months of treatment, the two patients stopped their treatment for lack of compliance after the death of their grandfather, while their mother had to be absent: they immediately underwent extensive rhabdomyolysis and were hospitalized in intensive care (CK 160 000 U/L and 300 000 U/L respectively). Since then they have resumed treatment. Throughout the winter 2016-2017 they did not do rhabdomyolysis and did not have muscle pain whereas winter is usually a difficult time for them.

REFERENCES

Throughout this application, various references describe the state of the art to which this invention pertains. The disclosures of these references are hereby incorporated by reference into the present disclosure.

1. Zeharia A, Shaag A, Houtkooper R H, et al. Mutations in LPIN1 cause recurrent acute myoglobinuria in childhood. *American journal of human genetics* 2008; 83(4): 489-94.

2. Michot C, Mamoune A, Vamecq J, et al. Combination of lipid metabolism alterations and their sensitivity to inflammatory cytokines in human lipin-1-deficient myoblasts. *Biochimica et biophysica acta* 2013; 1832(12): 2103-14.

3. Michot C, Hubert L, Brivet M, et al. LPIN1 gene mutations: a major cause of severe rhabdomyolysis in early childhood. *Human mutation* 2010; 31(7): E1564-73.

4. Michot C, Hubert L, Romero N B, et al. Study of LPIN1, LPIN2 and LPIN3 in rhabdomyolysis and exercise-induced myalgia. *Journal of inherited metabolic disease* 2012.

5. Bergounioux J, Brassier A, Rambaud C, et al. Fatal rhabdomyolysis in 2 children with LPIN1 mutations. *The Journal of pediatrics* 2012; 160(6): 1052-4.

6. Reue K. The lipin family: mutations and metabolism. *Current opinion in lipidology* 2009; 20(3): 165-70.

7. Jaber N, Mohd-Naim N, Wang Z, et al. Vps34 regulates Rab7 and late endocytic trafficking through recruitment of the GTPase-activating protein Armus. *Journal of cell science* 2016; 129(23): 4424-35.

8. Bento C F, Puri C, Moreau K, Rubinsztein D C. The role of membrane-trafficking small GTPases in the regulation of autophagy. *Journal of cell science* 2013; 126(Pt 5): 1059-69.

9. Guerra F, Bucci C. Multiple Roles of the Small GTPase Rab7. *Cells* 2016; 5(3).

10. Gutierrez M G, Munafo D B, Beron W, Colombo M I. Rab7 is required for the normal progression of the autophagic pathway in mammalian cells. *Journal of cell science* 2004; 117(Pt 13): 2687-97.

11. Jager S, Bucci C, Tanida I, et al. Role for Rab7 in maturation of late autophagic vacuoles. *Journal of cell science* 2004; 117(Pt 20): 4837-48.

12. Yao M, Liu X, Li D, Chen T, Cai Z, Cao X. Late endosome/lysosome-localized Rab7b suppresses TLR9-ini-

TABLE 1

Physical maximum capacities of two patients treated by Plaquenil ®.

| Patients 1 and 2 | M 0 | M 2 | M 5 | M 6-M 8 interruption ttt; M 9: | M 16 treatment |
|---|---|---|---|---|---|
| Six-minute walk test (normal 560-740) | P1: 450 m P2: 510 m | P1: 540 m P2: 550 m | P1: 520 m P2: 595 m | P1: 539 m P2: 587 m | P1: 530 P2: 590 |
| Questionnary (0: very well - 92: very bad) PESDQL children | P1: 26 P2: 45 | P1: 12 P2: 32 | P1: 11 P2: 35 | P1: 38 P2: 47 | P1: 8 P2: 30 |
| Questionnary PESDQL parent (0: very well - 92: very bad) | P1: 30 P2: 40 | P1: 22 P2: 42 | P1: 12 P2: 33 | P1: 31 P2: 50 | P1: 20 P2: 35 |
| Pain Evaluation (EVA) (4: not painful - 40: very painful) | P1: 24 P2: 18 | P1: 16 P2: 12 | P1: 0 P2: 0 | P1: 4 P2: 16 | P1: 0 P2: 0 | tiated proinflammatory cytokine and type I IFN production in macrophages. *Journal of immunology* 2009; 183(3): 1751-8.

13. Wang Y, Chen T, Han C, et al. Lysosome-associated small Rab GTPase Rab7b negatively regulates TLR4 signaling in macrophages by promoting lysosomal degradation of TLR4. *Blood* 2007; 110(3): 962-71.

14. Ge W, Li D, Gao Y, Cao X. The Roles of Lysosomes in Inflammation and Autoimmune Diseases. *International reviews of immunology* 2014.

15. Bucci C, Bakke O, Progida C. Rab7b and receptors trafficking. *Communicative & integrative biology* 2010; 3(5): 401-4.

16. Klaver E J, van der Pouw Kraan T C, Laan L C, et al. Trichuris suis soluble products induce Rab7b expression and limit TLR4 responses in human dendritic cells. *Genes and immunity* 2015.

17. Zhang Q, Raoof M, Chen Y, et al. Circulating mitochondrial DAMPs cause inflammatory responses to injury. *Nature* 2010; 464(7285): 104-7.

18. Oka T, Hikoso S, Yamaguchi O, et al. Mitochondrial DNA that escapes from autophagy causes inflammation and heart failure. *Nature* 2012; 485(7397): 251-5.

19. Bao W, Xia H, Liang Y, et al. Toll-like Receptor 9 Can be Activated by Endogenous Mitochondrial DNA to Induce Podocyte Apoptosis. *Sci Rep* 2016; 6: 22579.

20. Zhong Z, Umemura A, Sanchez-Lopez E, et al. NF-kappaB Restricts Inflammasome Activation via Elimination of Damaged Mitochondria. *Cell* 2016; 164(5): 896-910.

21. Lood C, Blanco L P, Purmalek M M, et al. Neutrophil extracellular traps enriched in oxidized mitochondrial DNA are interferogenic and contribute to lupus-like disease. *Nature medicine* 2016; 22(2): 146-53.

22. de Bernard M, Rizzuto R. Toll-like receptors hit calcium. *EMBO reports* 2014; 15(5): 468-9.

23. Shintani Y, Drexler H C, Kioka H, et al. Toll-like receptor 9 protects non-immune cells from stress by modulating mitochondrial ATP synthesis through the inhibition of SERCA2. *EMBO reports* 2014; 15(4): 438-45.

24. Shintani Y, Kapoor A, Kaneko M, et al. TLR9 mediates cellular protection by modulating energy metabolism in cardiomyocytes and neurons. *Proceedings of the National Academy of Sciences of the United States of America* 2013; 110(13): 5109-14.

25. Onoue K, Jofuku A, Ban-Ishihara R, et al. Fis1 acts as a mitochondrial recruitment factor for TBC1D15 that is involved in regulation of mitochondrial morphology. *Journal of cell science* 2013; 126(Pt 1): 176-85.

26. Yamano K, Fogel A I, Wang C, van der Bliek A M, Youle R J. Mitochondrial Rab GAPs govern autophagosome biogenesis during mitophagy. *eLife* 2014; 3: e01612.

27. Peralta E R, Martin B C, Edinger A L. Differential effects of TBC1D15 and mammalian Vps39 on Rab7 activation state, lysosomal morphology, and growth factor dependence. *The Journal of biological chemistry* 2010; 285(22): 16814-21.

The invention claimed is:

1. A method for determining whether a patient suffering from rhabdomyolysis achieves a response with a TLR9 antagonist and treating the patient, comprising:
   (i) determining the amount of mitochondrial DNA (mtDNA) in a blood sample obtained from the patient;
   (ii) comparing the amount determined at step (i) with a predetermined reference value; and
   (iii) concluding that the patient achieves a response when the amount determined at step (i) is lower that the predetermined reference value, treating the patient with the TLR9 antagonist.

2. A method of claim for monitoring compliance of a patient being treated for rhabdomyolysis with a TLR9 antagonist, comprising:
   (i) determining the amount of mitochondrial DNA (mtDNA) in a blood sample obtained from the patient;
   (ii) comparing the amount determined at step (i) with a predetermined reference value obtained from the patient after treatment began; and
   (iii) treating the patient with the TLR9 antagonist when an increase in the mtDNA compared to the predetermined reference value is detected, wherein the increase shows that the patient has failed to comply with the prescribed treatment.

3. The method of claim 1, wherein the TFRL9 TLR9 antagonist is hydroxychloroquine.

4. The method of claim 1, wherein the blood sample is a plasma sample.

5. The method of claim 1, wherein the quantification of mtDNA is performed by immunofluorescence or by PCR.

* * * * *